United States Patent [19]
Marie de Wit

[11] Patent Number: 5,866,776
[45] Date of Patent: Feb. 2, 1999

[54] METHOD FOR THE PROTECTION OF PLANTS AGAINST PATHOGENS

[75] Inventor: Peter Jozef Gerard Marie de Wit, Rhenen, Netherlands

[73] Assignee: Mogen International N.V., Netherlands

[21] Appl. No.: 199,984

[22] Filed: Feb. 22, 1994

Related U.S. Application Data

[63] Continuation of Ser. No. 777,400, filed as PCT/NL91/00052 Mar. 27, 1991, abandoned.

[30] Foreign Application Priority Data

Apr. 2, 1990 [NL] Netherlands ............................ 9000773

[51] Int. Cl.$^6$ .............................. C12N 5/00; C12N 15/00; A01H 1/04; C07H 21/04
[52] U.S. Cl. .................. 800/205; 435/172.3; 435/320.1; 536/23.74
[58] Field of Search .............................. 435/172.3, 320.1, 435/375; 536/23.6, 23.74, 24.1, 23.7; 800/205; 935/6, 35, 36

[56] References Cited

FOREIGN PATENT DOCUMENTS 0337532  10/1989  European Pat. Off. .
8605516   9/1986  WIPO .

OTHER PUBLICATIONS

R. Dixon et al. Annu. Rev. Plant Physiology Plant Mol. Biology, vol. 41 ('90) pp. 339–367.
C. Marineua et al. Plant Molecular Biology, vol. 9 ('87) pp. 335–342.
I. Somssich et al. Mol. Gen Genet., vol. 213 ('88) pp. 93–98.
K. Hahlbrock et al., Annu. Rev. Plant Physiol. Plant Mol. Biol., vol. 40 ('89) pp. 347–369.
L. Hoffman et al. Plant Mol. Biology, vol. 11, ('88) pp. 717–729.
I. Schorrens–Toma et al., Physiol. & Mol. Plant Pathology, vol. 33 ('88) pp. 59–67.
Dewit et al. Foundation for Biotech & Indust. Fermert. Res., vo. 6 ('89) pp. 221–236.
D. Baulcombe Trends in Genetics, vol. 5, No. 2 ('89) pp. 56–60.
R. Dixon et al., Ann. Rev. Plant Phys. & Mol. Biol. 41:339–67 ('90).
M. Joosten et al. Nature, vol. 367 (Jan. 27, 1994) pp. 384–386.
Dixon, R., et al. Ann. Rev. Plant Physiol. & Mol. Biol., vol. 41 (1990) pp. 339–367.
Douglas, C. J., et al. EMBO J., vol. 10 (1991) pp. 1767–1768.
Marineau, C., et al. Plant Molec. Biol., vol. 9 (1987) pp. 335–342.
Somssich, I. E., et al. Mol. Gen. Genet., vol. 213 (1988) pp. 93–98.
Hahlbrock, K., et al. Ann. Rev. Plant Physiol, vol. 40 (1989) pp. 347–369.
Biological Abstracts, vol. 91, 1991, J.A.L. Van Kan et al.: p. 499, abstract No. 72989.
Trends in Genetics, vol. 5, No. 2, Feb. 1989, pp. 56–60 of D. Baulcombe.
Physiological and Molecular Plant Pathology, vol. 33, No. 1, 1988, pp. 59–67, By I.M.J. Schottens–Toma et al.
Molecular Genetics of Plants–Microbe Interactions of 15–20 May 1988, By R.P. Oliver et al., pp. 263–265.
Foundation for Biotechnical and Industrial Fermentation Research, vol. 6, of 2–7 Jul. 1989, F.J.G.B. De Wit et al.

*Primary Examiner*—Bruce R. Campbell
*Attorney, Agent, or Firm*—Bachman & Lapointe, P.C.

[57] ABSTRACT

A method for the protection of plants against pathogens, wherein a polynucleotide sequence comprising at least a sequence of a pathogenic avirulence gene (E) encoding a specific elicitor protein molecule (e) or a portion thereof is introduced into the genome of a plant containing a corresponding resistance gene (R), in which genes (E) and (R) are regulated in such a manner that simultaneous expression of said genes only occurs at the site of infection and said simultaneous expression can be induced by a broad range of pathogens. A polynucleotide sequence comprising at least a sequence of an avirulence gene (E) from a plant pathogen encoding a specific elicitor protein molecule (e) or a portion thereof, and a plant promoter (P) that can be induced by a broad range of pathogens and which permits expression at the site of infection only. Plant obtainable by use of said method and plant comprising said polynucleotide sequence.

31 Claims, 4 Drawing Sheets

Oligonucleotide probes with corresponding amino acid sequence

| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 |
|---|---|---|---|---|---|---|---|---|---|---|---|---|---|---|---|---|---|---|---|---|---|---|---|---|---|---|
| Tyr | Cys | Asn | Ser | Cys | Thr | Arg | Ala | Phe | Asp | Phe | Cys | Leu | Gly | Gly | Cys | Gly | Arg | Cys | Asp | Phe | His | Lys | Leu | Gln | Cys | Val |
| UAU | UGU | AAU | UCU | UGU | ACU | CGU | GCU | UUU | GAU | UUU | UGU | CUU | GGU | GGU | UGU | GGU | CGU | UGU | GAU | UUU | CAU | AAA | CUU | CAA | UGU | GUU |
| C | C | C | UCU | C | C | C | C | C | C | C | C | C | C | C | C | C | C | C | C | C | C | G | C | G | C | C |
|   |   |   | A | A | A | A | A |   | C | C | A | A | A | A | A | A | A | A | C | C | C |   | G |   |   | A |
|   |   |   | G | G | G | G | G |   |   |   | G | G | G | G | G | G | G | G |   |   |   |   | UUA |   |   | G |
|   |   |   | AGU | C | AGA |   |   |   |   |   |   | UUA |   |   |   | AGA |   |   |   |   |   |   |   |   |   |   |
|   |   |   | C |   | G |   |   |   |   |   |   | G |   |   |   | G |   |   |   |   |   |   |   |   |   |   |

PROBE A:  5'  CC ACA TTG ICC IAG ACA ATC AAA  3'  (a.z. 10–17)
                           G    C          A   G    G    G

PROBE B:  5'  AG TTT ATG AAA ATC ACA  3'  (a.z. 19–24)
                   A   C    G    G    G    G

PROBE C:  5'  AC ICA ITG IAG TTT ATG AAA ATC ACA  3'  (a.z. 19–27)
                           A    C    G    G    G    G    G

PROBE D:  5'  AC ICA ITG IAI ITT ITG IAA ITC ICA  3'  (a.z. 19–27)

*FIG. 1*

Sequence of avr9 mRNA and the structure of the corresponding cDNA clones

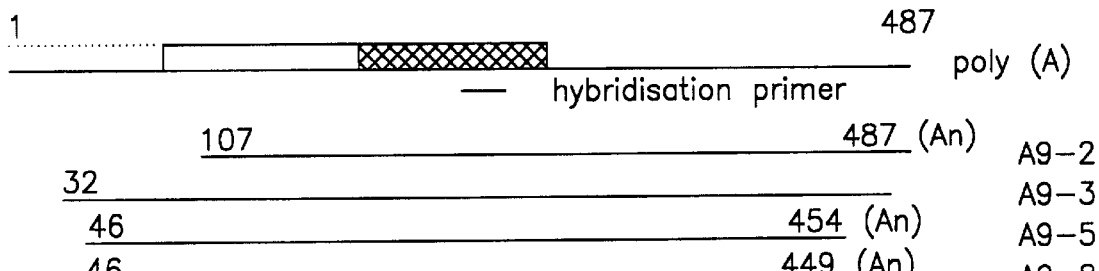

```
                                                                   M  K  L  S  L  L  S  V  E  L  A
  1 AACACTACGAATTTCGAAAAATCCTCAAGCCTACTAAGGTCTTTGTAGCCATAGTCATTT    60
 61 TAATAAGTCTATCGACTTACGTATCTATCATGAAGCTTTCCCTCCTTAGCGTAGAGCTTG   120

L  L  I  A  T  T  L  P  L  C  W  A  A  A  L  P  V  G  L  G
121 CTCTCCTAATTGCTACTACTCTCCCACTTTGCTGGGCAGCTGCCCTCCCTGTAGGATTGG   180

V  G  L  D  Y  C  N  S  S  C  T  R  A  F  D  C  L  G  Q  C
181 GAGTCGGGCTAGACTACTGTAACTCAAGTTGTACTAGGGCCTTCGACTGTTTGGGTCAAT   240

G  R  C  D  F  H  K  L  Q  C  V  H
241 GTGGCAGATGCGACTTTCATAAGCTACAATGTGTCCACTAGAGGACTAGAGAGGAAGTGG   300

301 AGAGAAGAGGAGGGGAGAGGTACGATAACTAGCGAGTAAATCGTACAGGTAGAAAGGGAT   360

361 AGTAAGCAGGCAGATAGACGGACGACGTTGCGACCTTATCCAACATAAGTCCTAGTCGTA   420

421 ACATTCGTTCATATTGAAGGCTTTTCCTCAATAGTTTCTCAAATGTGCTGCGAGGCGCAG   480

481 AGCCAAG   487
```

FIG. 4

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 81 base pairs
( B ) TYPE: nucleic acid
( C ) STRANDEDNESS: single
( D ) TOPOLOGY: linear ( i i ) MOLECULE TYPE: mRNA ( i i i ) HYPOTHETICAL: NO ( i v ) ANTI-SENSE: NO ( v ) FRAGMENT TYPE: C-terminal ( v i ) ORIGINAL SOURCE:
      ( A ) ORGANISM: Cladosporium fulvum
      ( B ) STRAIN: Cf5

( i x ) FEATURE:
      ( A ) NAME/KEY: CDS
      ( B ) LOCATION: 1..81
      ( D ) OTHER INFORMATION: /product="mature avr9"

( x i ) SEQUENCE DESCRIPTION: SEQ ID NO:1:

```
UAU  UGU  AAU  UCU  UCU  UGU  ACU  CGU  GCU  UUU  GAU  UGU  CUU  GGU  CAA  UGU      48
Tyr  Cys  Asn  Ser  Ser  Cys  Thr  Arg  Ala  Phe  Asp  Cys  Leu  Gly  Gln  Cys
 1                    5                        10                       15

GGU  CGU  UGU  GAU  UUU  CAU  AAA  CUU  CAA  UGU  GUU                               81
Gly  Arg  Cys  Asp  Phe  His  Lys  Leu  Gln  Cys  Val
                20                       25
```

( 2 ) INFORMATION FOR SEQ ID NO:2:

( i ) SEQUENCE CHARACTERISTICS:
            ( A ) LENGTH: 27 amino acids
            ( B ) TYPE: amino acid
            ( D ) TOPOLOGY: linear ( i i ) MOLECULE TYPE: protein ( x i ) SEQUENCE DESCRIPTION: SEQ ID NO:2:

```
Tyr  Cys  Asn  Ser  Ser  Cys  Thr  Arg  Ala  Phe  Asp  Cys  Leu  Gly  Gln  Cys
 1                    5                        10                       15

Gly  Arg  Cys  Asp  Phe  His  Lys  Leu  Gln  Cys  Val
                20                       25
```

( 2 ) INFORMATION FOR SEQ ID NO:3:

( i ) SEQUENCE CHARACTERISTICS:
            ( A ) LENGTH: 23 base pairs
            ( B ) TYPE: nucleic acid
            ( C ) STRANDEDNESS: single
            ( D ) TOPOLOGY: linear ( i i ) MOLECULE TYPE: nucleic acid probe ( i i i ) HYPOTHETICAL: NO ( x i ) SEQUENCE DESCRIPTION: SEQ ID NO:3:

```
CCRCAYTGNC  CNARRCARTC  RAA                                                         23
```

( 2 ) INFORMATION FOR SEQ ID NO:4:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( i i ) MOLECULE TYPE: nucleic acid probe ( i i i ) HYPOTHETICAL: NO ( x i ) SEQUENCE DESCRIPTION: SEQ ID NO:4:

```
ARYTTRTGRA  ARTCRCA                                                                 17
```

( 2 ) INFORMATION FOR SEQ ID NO:5:

( i ) SEQUENCE CHARACTERISTICS:
            ( A ) LENGTH: 26 base pairs
            ( B ) TYPE: nucleic acid
            ( C ) STRANDEDNESS: single
            ( D ) TOPOLOGY: linear (i i) MOLECULE TYPE: nucleic acid probe (i i i) HYPOTHETICAL: NO (x i) SEQUENCE DESCRIPTION: SEQ ID NO:5:

ACNCANTGNA RYTTRTGRAA RTCRCA 26

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (i i) MOLECULE TYPE: nucleic acid probe (i i i) HYPOTHETICAL: NO (x i) SEQUENCE DESCRIPTION: SEQ ID NO:6:

ACNCANTGNA NNTTNTGNAA NTCNCA 26

(2) INFORMATION FOR SEQ ID NO:7:

(i) SEQUENCE CHARACTERISTICS:
        (A) LENGTH: 486 base pairs
        (B) TYPE: nucleic acid
        (C) STRANDEDNESS: double
        (D) TOPOLOGY: linear (i i) MOLECULE TYPE: cDNA to mRNA (i i i) HYPOTHETICAL: NO (v i) ORIGINAL SOURCE:
        (A) ORGANISM: Cladosporium fulvum
        (B) STRAIN: Cf5

(v i i) IMMEDIATE SOURCE:
        (A) LIBRARY: lambda gt11
        (B) CLONE: A9-2

(i x) FEATURE:
        (A) NAME/KEY: CDS
        (B) LOCATION: 89..277

(i x) FEATURE:
        (A) NAME/KEY: CDS
        (B) LOCATION: 89..277
        (D) OTHER INFORMATION: /codon_start= 89
            / function= "elicitor protein"
            / product= "avr9"
            / gene= "avr9"

(x i) SEQUENCE DESCRIPTION: SEQ ID NO:7:

```
AACACACGAA TTTCGAAAAA TCCTCAAGCC TACTAAGGTC TTTGTAGCCA TAGTCATTTT           60

AATAAGTCTA TCGACTTACG TATCTATC ATG AAG CTT TCC CTC CTT AGC GTA            112
                              Met Lys Leu Ser Leu Leu Ser Val
                               1               5

GAG CTT GCT CTC CTA ATT GCT ACT ACT CTC CCA CTT TGC TGG GCA GCT           160
Glu Leu Ala Leu Leu Ile Ala Thr Thr Leu Pro Leu Cys Trp Ala Ala
     10              15                  20

GCC CTC CCT GTA GGA TTG GGA GTC GGG CTA GAC TAC TGT AAC TCA AGT           208
Ala Leu Pro Val Gly Leu Gly Val Gly Leu Asp Tyr Cys Asn Ser Ser
 25              30              35                          40

TGT ACT AGG GCC TTC GAC TGT TTG GGT CAA TGT GGC AGA TGC GAC TTT           256
Cys Thr Arg Ala Phe Asp Cys Leu Gly Gln Cys Gly Arg Cys Asp Phe
             45                  50                      55

CAT AAG CTA CAA TGT GTC CAC TAGAGGACTA GAGAGGAAGT GGAGAGAAGA              307
His Lys Leu Gln Cys Val His
```

```
                        60
GGAGGGGAGA  GGTACGATAA  CTAGCGAGTA  AATCGTACAG  GTAGAAAGGG  ATAGTAAGCA      367

GGCAGATAGA  CGGACGACGT  TGCGACCTTA  TCCAACATAA  GTCCTAGTCG  TAACATTCGT      427

TCATATTGAA  GGCTTTTCCT  CAATAGTTTC  TCAAATGTGC  TGCGAGGCGC  AGAGCCAAG       486
```

( 2 ) INFORMATION FOR SEQ ID NO:8:

( i ) SEQUENCE CHARACTERISTICS:
        ( A ) LENGTH: 63 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met  Lys  Leu  Ser  Leu  Leu  Ser  Val  Glu  Leu  Ala  Leu  Leu  Ile  Ala  Thr
 1              5                        10                       15

Thr  Leu  Pro  Leu  Cys  Trp  Ala  Ala  Ala  Leu  Pro  Val  Gly  Leu  Gly  Val
              20                       25                       30

Gly  Leu  Asp  Tyr  Cys  Asn  Ser  Ser  Cys  Thr  Arg  Ala  Phe  Asp  Cys  Leu
              35                       40                       45

Gly  Gln  Cys  Gly  Arg  Cys  Asp  Phe  His  Lys  Leu  Gln  Cys  Val  His
         50                       55                       60
```

METHOD FOR THE PROTECTION OF PLANTS AGAINST PATHOGENS

This is a continuation of application Ser. No. 777,400 filed on Dec. 02, 1991 now abandoned.

The invention is directed at a method for the protection of plants against pathogens, also at a polynucleotide sequence comprising an avirulence gene (E) from a pathogen regulated by a pathogen inducible promoter, and at a polynucleotide sequence comprising a corresponding resistance gene (R) regulated by a pathogen inducible promoter, whereby said DNA-sequences can be used in said method. The invention is also directed at a plant obtained via said method.

During evolution many fungi and bacteria that are pathogenic for plants have specialised in only one host species or sometimes even in one variety of said species. Thus pathogenic races can be found that colonise only certain cultivars of the host and do not colonise other cultivars. In the latter case the cultivars are resistant by means of a quick inducible defence mechanism.

In order to carry out a successful colonisation of the plant the pathogen must evade, suppress or nullify the existing defence mechanism of the plant. In genetic terms the specific race cultivar interactions can be described by a gene-for-gene model, whereby a protein elicitor molecule (e) encoded by a pathogen avirulence gene (E) interacts with a receptor protein molecule (r) encoded by a plant resistance gene (R) and thereby induces the defence mechanism, which often becomes phenotypically visible as the hypersensitive response (HR): the local death of a few plant cells, which simultaneously destroys the pathogen (De Wit, 1986).

The genetics of gene-for-gene interactions have been well described in the literature, especially the interactions between pathogenic fungi and plants (I. R. Crute, 1985), yet very little is known about the biochemical and molecular mechanisms (De Wit, 1987, Collinge and Slusarenko, 1987).

A pathogen that does not possess the avirulence gene or a pathogen in which the avirulence gene is not expressed does not trigger the host defence system and subsequently a successful colonisation can occur: in this case the host plant is susceptible.

Various race specific avirulence genes have been cloned from various plant pathogenic bacteria, whereby virulent races have been transformed with genomic clones of avirulent races and were subsequently tested for avirulence on plant genotypes with the corresponding resistance gene (Staskawicz et al., '84, Staskawicz et al. '87, Shintaku M. W. et al., '89, Vivian et al. '80, Hitchin et al. '89). This method of isolation of bacterial avirulence genes is however not applicable for fungal avirulence genes due to the low transformation efficiency and the lack of suitable cloning systems, such as cosmid vectors with a broad host range. The only fungus for which an efficient transformation system with an autonomously replicating vector has been determined is *Ustilago maydis* (Leong, 1989).

SUMMARY OF THE INVENTION

According to the invention, a method is provided for protecting plants against a pathogen, wherein the method comprises introducing, into a genome of the plant, a polynucleotide sequence comprising a translational initiation region followed by an open reading frame encoding a precursor of a specific elicitor protein (e) from a plant pathogen, and a promotor (p) from a plant gene which is inducible by said pathogen and expressed around a pathogen infection site of the plant, wherein the specific elicitor protein (e) corresponds to a resistance gene (R) present in the genome of the plant and includes a signal peptide part and mature peptide part, wherein the resistance gene (R) is effective to mediate resistance of the plant to the pathogen and wherein the promotor is operatively linked to the open reading frame so as to allow transcription and translation of the open reading frame.

BRIEF DESCRIPTION OF THE DRAWINGS

A detailed description of preferred embodiments of the invention follows, with reference to the attached drawings wherein:

FIG. 1 shows amino acid sequences for oligonucleotide probes for the following examples;

FIG. 4 shows the sequence of Avr9 cDNA and the structure of corresponding cDNA-clones.

DETAILED DESCRIPTION

Figure 2:
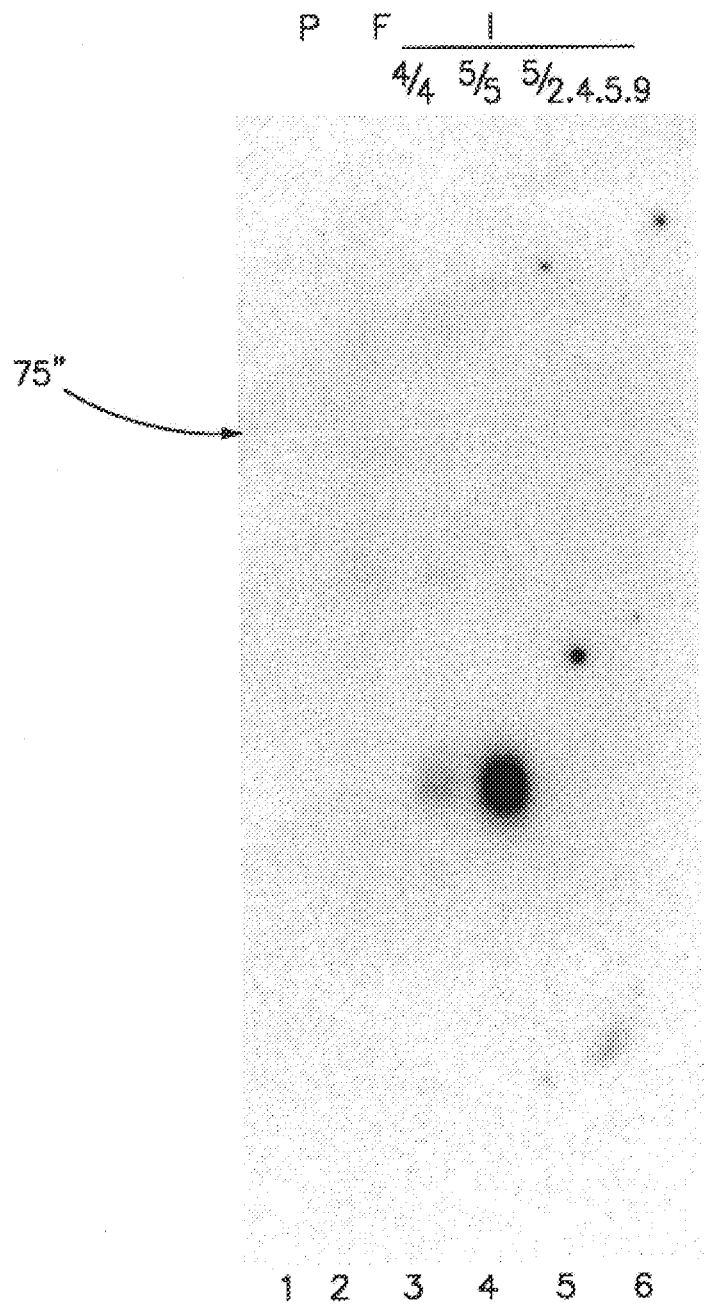
FIG. 2 shows oligonucleotide hybridization for several interactions.

It has been found that plants can be offered a broad protection against pathogens by introducing a polynucleotide sequence comprising at least a sequence of a pathogen avirulence gene (E) encoding a specific elicitor protein molecule (e) or a portion thereof, into the genome of a plant containing a corresponding resistance gene (R), and providing means for regulating the expression of said genes in such a manner that simultaneous expression occurs only at the site of infection and induction of said simultaneous expression can be achieved by a broad range of pathogens.

It is possible to introduce the above-mentioned polynucleotide sequence comprising at least a sequence of a pathogen avirulence gene (E) into a plant that contains resistance gene (R) that is at least expressed at the site of infection, putatively even constitutively in the whole plant. In this case the avirulence gene (E) must be regulated by a promoter that is induced by a pathogen and only permits expression at the site of infection, in order to avoid the induction of the hypersensitive response in the whole plant.

The hypersensitive response is only permitted to be activated by a pathogen or an aspecific elicitor produced by a pathogen. The hypersensitive response must not or hardly be inducible by other exterior stimuli and should be restricted to an area surrounding the site of infection. Without these restrictions the activation would result in the virtual destruction of the plant.

It is also possible to introduce a resistance gene (R) corresponding to the avirulence gene (E) into a plant that does not already contain the corresponding resistance gene (R). This can be achieved via breeding or via genetic manipulation techniques.

In the latter case it is possible to introduce a polynucleotide sequence comprising at least a sequence of a resistance gene (R) or a portion thereof, and a plant promoter (P) that can be induced by a broad range of pathogens and in such a manner that the product of resistance gene (R) is only expressed at the site of the infection. In this instance it is even possible for the avirulence gene (E) to be constitutively expressed even in the whole plant. It is also possible for gene (E) and gene (R) to be regulated by identical promoters provided they are strictly inducible at the site of the infection and only by a pathogen.

In the above mentioned embodiments the pathogen-inducible promoter to be employed is required to:

a) be induced by all or most of the plant's pathogens or aspecific elicitors produced by said pathogens;
b) be virtually only inducible by pathogens and not or hardly inducible by other exterior stimuli;
c) be only able to express the genes that are controlled by the promoter very locally and never systemically.

In another embodiment of the invention gene (E) or (R) can be tissue specific and the other gene must be pathogen inducible at the site of the infection only in tissue for which the first gene is tissue specific. In this instance it is for example possible to introduce a gene (R) that is expressed only in the roots of the plant and a gene (E) that is induced locally by a pathogen in the roots yet constitutively in other tissues, whereby protection against pathogens is obtained for the roots.

The avirulence gene (E) can be derived from a fungus, a bacterium, a virus or a nematode. An example of a plant pathogenic fungus from which an avirulence gene can be readily derived is *Cladosporium fulvum*.

The resistance gene (R) can be used that is naturally present for example in a plant that is a member of the family of the Solanaceae, such as a plant of the species *Lycopersicon esculentum*. It is possible to introduce this gene (R) into another member of the family of the Solanaceae by breeding. Said other member can either already contain the stringently regulated avirulence gene (E) or else said avirulence gene can be subsequently introduced into the plant via genetic manipulation techniques. The resistance gene (R) can obviously also be introduced via genetic manipulation techniques.

The choice of the combination of avirulence gene (E) and resistance gene (R) as well as the promoters to be introduced into the plant, be it through breeding or genetic manipulation techniques, will depend on the plant variety that is to be protected and whether resistance gene (R) is naturally present in the plant.

In the whole plant kingdom pathogen inducible plant promoters are known that are induced by a broad range of pathogens and by aspecific elicitors produced by these pathogens. Such plant promoters are also known that are only expressed very locally and never systemically. Matton and Brisson (1989), for example describe the nucleotide sequence of a cDNA clone (pSTH-2) corresponding to mRNA sequences that specifically accumulate in potato after elicitation with nonspecific elicitors of *P. infestans* (Marineau et al., 1987), as well as a closely related clone, pSTH-21, that shows great similarity in amino acid sequence with the cDNA-clones corresponding to the elicitor and pathogen induced pathogenesis related proteins from the pea (42%) (Fritensky et al., 1988) and parsley (37%) (Somsisch 1988). Matton and Brisson (1989) also describe the accumulation of mRNA's corresponding to said clones pSTH-2 and pSTH-21 in various potato tissues and in tomato leaves. Somsisch (1986) describes how the de novo synthesis of pathogenesis related (PR) proteins in cultured parsley cells can be achieved by treatment with fungal elicitor. In this system PR-protein synthesis is preceded by mRNA synthesis resulting from fast and temporary activation of the corresponding genes. Such activation is also observed with intact parsley plants upon fungal infection (Somsisch, 1988) and is accompanied by massive yet local accumulation of mRNA around the infection sources. In general genes involved in the synthesis of phytoalexins are induced very locally in plants by various types of pathogens and their specific elicitors (Hahlbrock, H. and Scheel, D., 1989; Kuc, J. and Rush, J. S., 1985). Examples of pathogenisis related (PR) genes containing suitable promoter nucleotide sequences include but are not limited to PRP genes from potato such as pSTH-2 and pSTH-21, genes corresponding with PR1 and PR2 from parsley, and PAL, 4CL and CHS genes coding for phytoalexin.

One of the methods that can be used for the detection of a resistance gene (R) from a plant, whereby the product (r) of said gene shows interaction with a specific elicitor protein molecule (e) that is encoded by a pathogen avirulence gene (E) can be described as follows; in this method a specific elicitor protein (e), a resistance gene product (r) and subsequently a resistance gene (R) are isolated with the aid of the product of an avirulence gene (E). In principle this method can be used for the isolation of any resistance gene product (r) and the encoding resistance gene (R) when the corresponding avirulence gene (E) and its product (e) are known. The method can be represented as follows; a cDNA-library of a plant containing the resistance gene (R) is made in an expression vector, whereby the product of (R), the receptor (r) is produced. A positive clone is detected in the cDNA-library by binding a specific elicitor protein molecule (e) to the receptor protein (r). The binding (complexing of (e) to (r)) is made visible by providing (e) with a detectable label. This positive cDNA-clone contains the coding sequence for the resistance gene. The intact gene (R) can be detected with this cDNA-clone from the genomic library from the plant containing the resistance gene. With the aid of the cDNA or genomic clone a plant lacking the resistance gene can be transformed; positive transformants are screened for possession of the resistance gene by inoculation (contamination) with the appropriate pathogen. The cloned gene (R) can be introduced into plants via either genetic manipulation techniques or breeding.

Alternatively the resistance gene (R) can be cloned by published methods of transposon tagging, chromosome walking and genomic substitution (Dickinson, M. D. et al, 1991).

It is highly unlikely that pathogens will develop tolerance to a plant comprising the two components, i.e. gene (E) and gene (R) (the two component sensor system), obtained via the method according to the invention, due to the use of aspecific inducible plant promoters, inducible by all pathogens, to induce the simultaneous local expression of the avirulence gene (E) and the resistance gene (R). It is necessary for at least one of the promoters regulating either the avirulence gene (E) or the resistance gene (R) to be only inducible at the site of the infection, in order to avoid destruction of virtually the whole plant, which is obviously undesirable.

As the two component sensor system according to the invention can be obtained with every combination of avirulence gene-resistance gene in any plant in which the avirulence gene and the resistance gene can be expressed, it is very broadly applicable against many if not all pathogens for the plant kingdom.

The two component sensor system provides an excellent solution to reduce the use of the pesticides now frequently used against pathogens. In time this will make it possible to relieve the environment of a large part of these agents.

By way of example, a description of the preparation of a two component sensor system according to the method of the invention is given.

EXAMPLE

An avirulence gene of *Cladosporium fulvum* (namely the avr9 avirulence gene, that was previously referred to in the literature as A9) is applied as avirulence gene in combination with the corresponding resistance gene Cf9, that is naturally present in a tomato cultivar. This two component sensor system can at least be propagated by breeding into varieties of the genus Lycopersicon and a part of the Solanaceae family and can optionally be introduced via genetic manipulation techniques in said plants or in other families. Various fungally encoded race specific elicitor molecules have been identified that induce necrosis on tomato cultivars containing the corresponding resistance genes (De Wit and Spikman 1982; De Wit et al. 1985). Such a race specific elicitor molecule, the product of avirulence gene avr9, has been purified to homogeneity. The purified protein induced fast and local necrosis upon injection into leaves of tomato genotypes containing the resistance gene Cf9. In genotypes containing other Cf-genes this did not occur. The amino acid sequence of the purified elicitor molecule was determined (Schottens-Toma and De Wit 1988). The elicitor molecule was formed in all compatible interactions between tomato-C. fulvum involving races of fungi that were avirulent on tomatoes Cf9 genotypes, however at no single interaction involving races of fungi that are virulent on Cf9 genotypes (Scholtens-Toma et al. 1989). In order to detect the mRNA encoding the necrosis inducing protein, i.e. an elicitor protein, 4 oligonucleotide probes were synthesised derived from the amino acid sequence (FIG. 1). The oligonucleotides contain either mixtures of nucleotides (such as in probe B) or inosines (such as in probe D) or a combination of both (such as in probes A and C). All four oligonucleotides were labelled at the 5'-terminus and hybridised to identical Northern blots containing identical amounts of poly(A)-RNA derived from healthy tomato plants, in vitro cultured C. fulvum and 3 different compatible tomato-C. fulvum interactions. FIG. 2 shows that probe B specifically hybridised to a mRNA of approximately 600 nucleotides that was present in two compatible interactions namely: cultivar Cf4/race 4 (lane 3) and cultivar Cf5-race 5 (lane 4). This mRNA was not found in tomato plants that were not infected (lane 1) or in C. fulvum cultivated in vitro (lane 2). Neither was any hybridisation observed in the interaction of cultivar Cf5 with race 2.4.5.9.11 (lane 5), as could be expected for an interaction of a race that is virulent on tomato Cf9 genotypes. Thus it was concluded that probe B detected mRNA for the necrosis inducing protein. Probes A, C and D did not detect specific mRNA's as is shown in FIG. 2.

Figure 3:
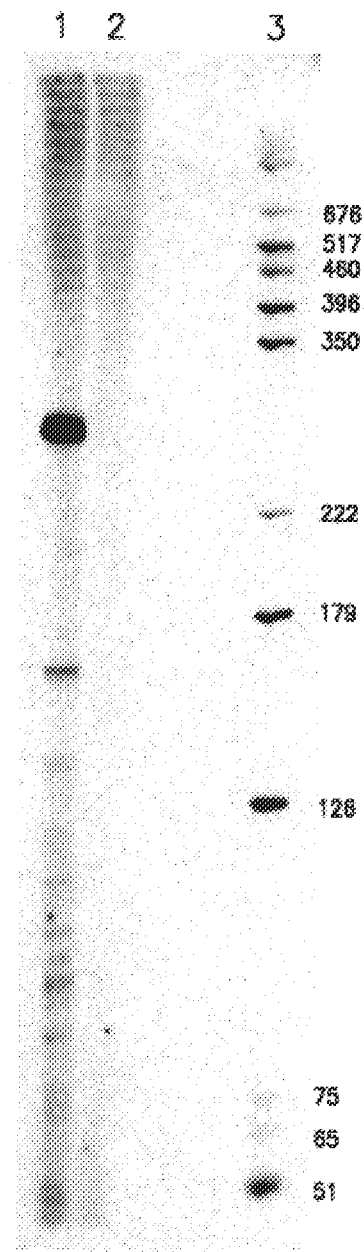
FIG. 3 shows specific extension products for poly (A)-RNA.

Oligonucleotide probe B was used in a primer-extension experiment. The oligonucleotide was labelled at the 5'-terminus and hybridised to equal amounts of poly(A)-RNA derived from compatible interactions of cultivar Cf5 with either race 5 or race 2.4.5.9.11 (represented respectively in FIG. 1, lanes 4 and 5). The primer was extended with reverse transcriptase and the extension products were analysed on a PAGE-gel. FIG. 3 shows that a specific extension product was formed on poly(A)-RNA derived from the interaction of cultivar Cf5/race 5 (lane 1), however not on poly(A)-RNA derived from the interaction of cultivar Cf5/race 2.4.5.9.11 (lane 2). The size of the extension product was approximately 270 nucleotides which indicated that avr9 mRNA possesses approximately 200 nucleotides for the sequence encoding the necrosis inducing protein.

Poly(A)-RNA derived from the interaction of Cf5/race 5 (represented in FIG. 2, lane 4) was used to prepare a cDNA library in lambda gt11. A library was obtained containing 100.000 independent recombinants. Examination of filters containing 5000 phages with terminally labelled oligonucleotide probe B, resulted in the isolation of two possible candidates, one that hybridised weakly (phage A9-1), and one that hybridised appreciably better (phage A9-2). Both phages were purified and the DNA was isolated. The phage DNA was labelled and hybridised to blots that were identical to the blot shown in FIG. 2. Phage A9-1 hybridised to an mRNA containing approximately 1500 nucleotides and was present in a small amount in the three interactions between tomato and C. fulvum. This phage did not contain cDNA corresponding to the mRNA observed in FIG. 2 and was not analysed further.

The labelled DNA of phage A9-2 hybridised with an mRNA of approximately 600 nucleotides that was only present in the compatible interactions of cultivar Cf4/race 4 and cultivar Cf5/race 5 i.e. in a pattern corresponding to the hybridisation observed with oligonucleotide probe B. Therefore phage A9-2 contained a copy of the mRNA encoding the necrosis inducing protein. The cDNA present in phage A9-2 was subcloned and the sequence was determined. The insertion had a length of 405 base pairs and corresponded to the 3'-terminus of the mRNA including a poly(A)-tail of 20 nucleotides. The insertion encoded the whole sequence of the necrosis inducing protein and was contained within a longer open reading frame. It was estimated from the position of the oligonucleotide probe B in the DNA sequence and the size of the primer extension product that the insertion of clone A9-2 lacked approximately 110 base pairs at the 5'-terminus of the mRNA. In order to obtain a full length cDNA-clone the cDNA-library was examined again with a labelled RNA-probe containing 70 nucleotides of the 5'-terminus of the insertion of clone A9-2. Three different phages A9-3, A9-5 and A9-8 were obtained and their insertions were subcloned and sequenced. The sequence of the three clones was completely identical to the sequence of clone A9-2 in the overlapping regions. The 4 clones contain poly(A)-tails commencing at different positions in the sequence. It was derived from the primer extension experiment shown in FIG. 3 that the largest clone (A9-3) lacked approximately 35 nucleotides. Therefore a new primer was designed that hybridised at position 75–100. This primer was used in a primer extension experiment on poly(A)-RNA in the presence of dideoxynucleotides. This RNA-sequence led to the addition of another 24 nucleotides in front of the insertion of A9-3. Other final products were observed that were 5–20 nucleotides longer than the major extension product. The various final products of the primer extension were not caused by degradation of mRNA, as one extension experiment with a primer for a different mRNA provided only one discrete extension product with the correct size. The sequence of the avr9 cDNA and the structure of the corresponding cDNA-clones is shown in FIG. 4. The isolation and characterisation of the cDNA-clones revealed that the necrosis inducing protein is formed as a precursor protein of at least 63 amino acids. Surprisingly the DNA sequence revealed an additional histidine codon at the C-terminus of the sequence of the mature elicitor molecule. It has previously been described that the elicitor molecule had a length of 27 amino acids (Scholtens-Toma and De Wit, 1988). Re-examination of the protein sequence data, however, confirmed the presence of an additional histidine residue at position 28. This residue had been overlooked during the original analysis of the protein sequence due to a low signal obtained with this amino acid. The molecular weight of the mature avr9 elicitor protein molecule is 3189 Dalton.

A genomic clone of the avirulence gene avr9 has been isolated from a genomic library (in vector lambdaEMBL3) of race 5 of C. fulvum using the cDNA clone A9-2. Sequence analysis revealed a 59 base pair intron, a putative TATA-box and several repeats in the promoter and terminator region.

Stable transformants of race 2.4.5.9.11 were obtained with the genomic clone after co-transformation with pAN7 (hygromycine resistance). The wild type race 2.4.5.9.11 is virulent on Cf9 genotypes of tomato but the transformant was not. This means that cultivar specificity of these transformants was converted phenotypically from virulent to avirulent on Cf9 genotypes, indicating that the avirulence gene avr9 has changed the genotype of race 2.4.5.9.11 into that of race 2.4.5.11. This experiment proves that avirulence gene avr9 is indeed the causal inducer of resistance in combination with the Cf9 resistance gene. Hence, it can be concluded that locally simultaneous expression of an avirulence gene (E) and a corresponding resistance gene (R) in a plant gives rise to local necrosis.

References

1. Collinge, D. B. and Slusarenko, A. J. 1987, Plant gene expression in response to pathogens, Plant Mol. Biol. 9, 389–410
2. Crute I. R. (1985). The genetic basis of relationships between microbial parasites and their hosts. “Mechanisms of resistance to plant diseases”, (Ed. Fraser R. S. S.), 80–142, M. Nijhoff/Dr. W. Junk Uitg. Mij., Dordrecht
3. De Wit P. J. G. M. and Spikman G. (1982), Physiol. Plant Pathol. 21, 1–11
4. Dickinson, M., Jones, D., Thomas, C., Harrison, K., Englisch, J., Bishop, G., Scofield, S., Hammond-Kosack and Jones, J. D. G. (1991) Strategies for the cloning of genes in tomato for resistance to *Fulvia fulva*. In: advances in Molecular Genetics of Plant-Microbe Interactions; Volume 1. (eds. Hennecke, H., Verma, D. S.) Kluwer Academic Publishers, Dordrecht, Boston, London.
5. Pristensky B., Horovitz D., and Hadwiger L. A. (1988). cDNA Sequences for pea disease resistance response genes. Plant Molecular Biology 11, 713–715
6. Hahlbrock, H. and Scheel, D., (1989) Physiology and molecular biology of phenylpropanoid metabolism. Annual Review of Plant Physiology and Plant Molecular Biology 40, p 347–369
7. Hitchin F. E. et al. (1989) Physiol. Molec. Plant Pathol. 35, 335–344.
8. Kuc, J. and Rush, J. S., (1985), Phytoalexins. Archives of Biochemistry and Biophysics 236, p455–472
9. Leong S. A. and Holden (1989), Annu. Rev. Phytopathol. 27, 463–481.
10. Marineau, C., Matton D. P., and Brisson, N. 1987. Differential Accumulation of potato tuber mRNA’s during the hypersensitive response induced by arachidonic acid elicitor. Plant Mol. Biol. 9, 335–342.
11. Matton D. P. en Brisson N. (1989). Cloning, expression, and sequence conservation of pathogenesis-related gene transcripts of potato. Molecular Plant-Microbe Interactions 2, 325–331.
12. Scholtens-Toma I. M. J., De Wit G. J. M. en De Wit P. J. G. M. (1989) Neth. J. Plant Pathol. 95, suppl. 1, 161–168.
13. Schottens-Toma I. M. J. and De Wit P. J. G. M. (1988) Physiol. Molec. Plant Pathol. 33, 59–67
14. Shintaku M. H. et al. (1989) Physiol. Molec. Plant Pathol. 35, 313–322.
15. Somssisch I. E., Schmelzer E., Bollmann J. and Hahlbrock K. 1986. Rapid activation by fungal elicitor of genes encoding “pathogenesis-related” proteins in cultured parsley cells. Proc. Natl. Acad. Sci. USA 83, 2427–2430.
16. Somssich I. E., Schmelzer E., Kawlleck P. en K. Hahlbrock (1988). Gene structure and in situ transcript localization of pathogenesis-related protein 1 in parsley. Molecular and General Genetics 213, 93–98.
17. Staskawicz B. J., Dahlbeck D., Keen N. T. (1984) Proc. Natl. Acad. Sci. USA 81, 6024–6028.
18. Staskawicz B. et al. (1987) J. Bacter. 169, 5789–5794.
19. Vivian A. et al. (1989) Physiol. Molec. Plant Pathol. 35, 335–344.
20. de Wit P. J. G. M. and Hofman J. E. and Velthuis G. C. M. and Kuc J. A. (1985) Plant fysiol. vol. 77, pp 642–647. Isolation and characterisation of an elicitor of necrosis isolated from intercellular fluids of compatible interactions of *Clad. fulvum* (*syn. fulvia, fulva*) and tomato.
21. de Wit P. J. G. M. -Specificity of active resistance mechanisms in plant-fungus interactions in: “Fungal infection of plants ed. G. F. Pegg and P. G. Ayres” pp 1–24, Cambridge University Press.
22. de Wit P. J. G. M. (1986) Elicitation of active resistance mechanisms. In: “Biology and molecular biology of plantpathogen interactions”. Editor J. Bailey. NATO ASI series, Volume H1, Springer Verlag. Berlin-Heidelberg, pp 149–169.

What is claimed is:

1. A method for protecting plants against a pathogen, comprising the steps of:
   providing a plant containing a resistance gene (R) which is effective to mediate plant resistance; and
   transforming the plant with a polynucleotide sequence encoding a pathogen-derived elicitor protein (e) which corresponds to the resistance gene (R), wherein expression of at least one of the resistance gene (R) and the elicitor protein (e) is regulated by a promotor (p) which is inducible by said pathogen and expressed at a pathogen infection site of the plant.

2. A method according to claim 1, wherein the promoter (p) is obtained from a member of the family Solanaceae.

3. A method according to claim 2, wherein the promoter (p) is obtained from the group consisting of members of the genus Lycopersicon and Solanum.

4. A method according to claim 1, wherein the specific elicitor protein (e) is derived from a plant pathogenic fungus.

5. A method according to claim 4, wherein the specific elicitor protein (e) is derived from *Cladosporium fulvum*.

6. A method according to claim 5, wherein the specific elicitor protein (e) is encoded by a pathogen avirulence gene (E) which is a portion of avr9 sufficient to cooperate with a corresponding receptor protein of the resistance gene (R) so as to induce a hypersensitive response.

7. A method according to claim 1, wherein the specific elicitor protein (e) is derived from a plant pathogenic bacterium.

8. A method according to claim 1, wherein the specific elicitor protein (e) is derived from a plant parasitic nematode.

9. A method according to claim 1, wherein the specific elicitor protein (e) is derived from a plant pathogenic virus.

10. A method according to claim 1, wherein resistance gene (R) is from a member of the family Solanaceae.

11. A method according to claim 10, wherein the resistance gene (R) is from a plant of the species *Lycopersicon esculentum*.

12. A method according to claim 11, wherein the resistance gene (R) is Cf9.

13. A polynucleotide sequence, comprising a translation initiation region followed by an open reading frame encoding a precursor of a specific elicitor protein (e) from a plant pathogen, wherein said plant pathogen is *Cladosporium fulvum*, and wherein the specific elicitor protein (e) comprises a signal peptide part and a mature elicitor peptide part.

14. A polynucleotide sequence according to claim 13, wherein the open reading frame encodes a precursor of the elictor protein avr9.

15. A polynucleotide sequence according to claim 13, wherein the precursor of the elicitor protein has a sequence as set forth in SEQ ID NO:7 of the sequence listing.

16. A polynucleotide sequence according to claim 13, further comprising a promoter (p) from a plant gene which is inducible by at least one pathogen and expressed at a pathogen infection site, the promoter being operatively linked to the open reading frame so as to allow transcription and translation of the open reading frame in a plant cell.

17. A polynucleotide sequence according to claim 16, wherein the promoter (p) is obtained from a plant pathogenesis-related protein gene.

18. A polynucleotide sequence according to claim 16, wherein the promoter (p) is obtained from a gene selected from the group consisting of genes corresponding with pSTH-2 and pSTH-21 from potato, genes corresponding with PR1 and PR2 from parsley, and plant genes coding for phytoalexin.

19. A plant having a recombinant plant genome, wherein the recombinant plant genome comprises a plant expressible gene encoding a precursor of a specific elicitor protein (e) from a plant pathogen, wherein said plant pathogen is *Cladosporium fulvum*, and wherein the plant genome further comprises a resistance gene corresponding to the specific elicitor protein and wherein the resistance gene is effective to mediate resistance of the plant to the pathogen.

20. A plant according to claim 19, wherein the elicitor protein is an avr9 protein from *Cladosporium fulvum*.

21. A plant according to claim 20, wherein the avr9 protein is encoded by an open reading frame having the sequence of SEQ ID NO:7 of the sequence listing.

22. A plant according to claim 19, further including a promoter (p) from a plant gene which is inducible by a pathogen and expressed around a pathogen infection site of a plant, the promoter (p) being operatively linked to an open reading frame of the plant expressible gene so as to allow transcription and translation of the open reading frame in a plant cell.

23. A plant including a recombinant plant genome comprising a plant expressible gene encoding a precursor of a specific elicitor protein (e), wherein said specific elicitor protein (e) is from a plant pathogen, and wherein said plant pathogen is *Cladosporium fulvum*, whereby the plant is less susceptible to pathogen attack.

24. A method according to claim 1, wherein the plant and the resistance gene (R) are from the same plant family.

25. A method according to claim 1, wherein the plant and the resistance gene (R) are from the Solanaceae family.

26. A method according to claim 1, wherein the plant and the resistance gene (R) are from the same species.

27. A method according to claim 1, wherein the plant and the resistance gene (R) are from the *Lycopersicon esculentum* species.

28. A method according to claim 5, wherein the specific elicitor protein (e) is an avr elicitor.

29. A method for protecting plants against a pathogen, comprising the steps of:

providing a plant; and transforming the plant with a polynucleotide sequence encoding a resistance gene (R) and a pathogen-derived elicitor protein (e) which corresponds to the resistance gene (R), wherein expression of at least one of the resistance gene (R) and the elicitor protein (e) is regulated by a promoter (p) which is inducible by said pathogen and expressed at a pathogen infection site of the plant.

30. A plant according to claim 19, wherein expression of at least one of the resistance gene (R) and the elicitor protein (e) is regulated by a promoter (p) which is inducible by said pathogen and expressed at a pathogen infection site of the plant.

31. A plant according to claim 23, wherein expression of the elicitor protein (e) is regulated by a promoter (p) which is inducible by said pathogen and expressed at a pathogen infection site of the plant.

\* \* \* \* \*